(12) United States Patent
Dolente et al.

(10) Patent No.: US 12,116,349 B2
(45) Date of Patent: Oct. 15, 2024

(54) METHYLQUINAZOLINONE DERIVATIVES

(71) Applicant: Hoffmann-La Roche Inc., Little Falls, NJ (US)

(72) Inventors: Cosimo Dolente, Allschwil (CH); David Stephen Hewings, Abingdon (GB); Daniel Hunziker, Mohlin (CH); Daniela Krummenacher, Zurich (CH); Piergiorgio Francesco Tommaso Pettazzoni, Regensdorf (CH); Juergen Wichmann, Steinen (DE)

(73) Assignee: Hoffmann-La Roche Inc., Little Falls, NJ (US)

( * ) Notice: Subject to any disclaimer, the term of this patent is extended or adjusted under 35 U.S.C. 154(b) by 259 days.

(21) Appl. No.: 17/835,245

(22) Filed: Jun. 8, 2022

(65) Prior Publication Data

US 2022/0298119 A1    Sep. 22, 2022

Related U.S. Application Data

(63) Continuation of application No. PCT/EP2020/084976, filed on Dec. 8, 2020.

(30) Foreign Application Priority Data

Dec. 10, 2019 (EP) .................................. 19214941

(51) Int. Cl.
*C07D 239/88* (2006.01)
*A61P 35/00* (2006.01)

(52) U.S. Cl.
CPC ............ *C07D 239/88* (2013.01); *A61P 35/00* (2018.01)

(58) Field of Classification Search
CPC ............................... C07D 239/88; A61P 35/00
See application file for complete search history.

(56) References Cited

U.S. PATENT DOCUMENTS

| | | | |
|---|---|---|---|
| 2016/0339025 A1 | 11/2016 | Ibrahim et al. | |
| 2022/0298119 A1 | 9/2022 | Dolente et al. | |
| 2022/0298145 A1* | 9/2022 | Dolente | A61P 35/00 |
| 2023/0322776 A1 | 10/2023 | Dolente et al. | |
| 2023/0331682 A1 | 10/2023 | Dolente et al. | |

FOREIGN PATENT DOCUMENTS

| | | |
|---|---|---|
| CN | 104640865 A | 5/2015 |
| CN | 116096710 A | 5/2023 |
| JP | 2018-515570 A | 6/2018 |
| RU | 2685250 C2 | 4/2019 |
| RU | 2687107 C1 | 5/2019 |
| WO | 2005/120210 A1 | 12/2005 |
| WO | 2007/065662 A2 | 6/2007 |
| WO | 2007/065663 A2 | 6/2007 |
| WO | 2009/012283 A1 | 1/2009 |
| WO | 2009/117080 A1 | 9/2009 |
| WO | 2010/084050 A2 | 7/2010 |
| WO | 2010/129567 A1 | 11/2010 |
| WO | WO-2012118492 A1 * | 9/2012 ........... C07D 239/74 |
| WO | 2014/018725 A1 | 1/2014 |
| WO | 2014/047020 A1 | 3/2014 |
| WO | 2014/194127 A1 | 12/2014 |
| WO | 2017/060874 A1 | 4/2017 |
| WO | 2020/142612 A1 | 7/2020 |
| WO | 2020/261156 A1 | 12/2020 |
| WO | 2021/116050 A1 | 6/2021 |
| WO | 2021/116055 A1 | 6/2021 |
| WO | 2021/250521 A1 | 12/2021 |
| WO | 2022/129259 A1 | 6/2022 |
| WO | 2022/129260 A1 | 6/2022 |
| WO | 2022/261250 A1 | 12/2022 |
| WO | 2023/105371 A1 | 6/2023 |

OTHER PUBLICATIONS

Durmas, S., et al., "Oral Availability and Brain Penetration of the B-RAFV600E Inhibitor Vemurafenib Can Be Enhanced by the P-Glycoprotein (ABCB1) and Breast Cancer Resistance Protein (ABCG2) Inhibitor Elacridar" ACS Mol Pharmaceutics 9(11):3236-3245 (Sep. 28, 2012).

Holderfield, M., et al., "Mechanism and consequences of RAF kinase activation by small-molecule inhibitors" BR J Cancer 111(4):640-645 (Aug. 12, 2014).

Holderfield, M., et al., "Targeting RAF kinases for cancer therapy: BRAF-mutated melanoma and beyond" Nat Rev Cancer 14(7):455-467 (Jul. 1, 2014).

"International Preliminary Report on Patentability—PCT/EP2020/084976" (Report Issuance Date: Mar. 7, 2022; Chapter II),:pp. 1-10 (Mar. 7, 2022).

"International Preliminary Report on Patentability—PCT/EP2020/084969" (Report Issuance Date: Mar. 7, 2022; Chapter II),:pp. 1-10 (Mar. 7, 2022).

"International Search Report—PCT/EP2020/084976" (w/Written Opinion),:pp. 1-14 (Feb. 23, 2021).

"International Search Report—PCT/EP2020/084969" (w/Written Opinion),:pp. 1-17 (Feb. 24, 2021).

(Continued)

*Primary Examiner* — Matthew P Coughlin
*Assistant Examiner* — Quincy McKoy
(74) *Attorney, Agent, or Firm* — Vasily Ignatenko

(57) ABSTRACT

The invention provides a novel compound having the general formula (I)

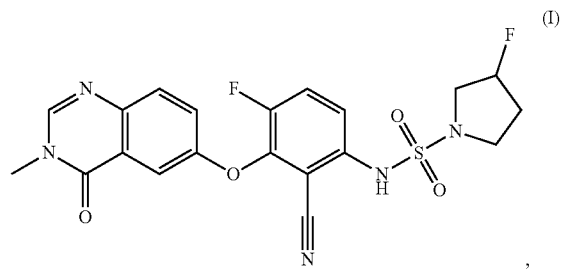

or a pharmaceutically acceptable salt thereof. The compound of formula (I) can be used as a medicament.

54 Claims, 8 Drawing Sheets

(56) References Cited

OTHER PUBLICATIONS

Mittapalli, R., et al., "Mechanisms limiting distribution of the threonine-protein kinase B-RaF(V600E) inhibitor dabrafenib to the brain: implications for the treatment of melanoma brain metastases" J Pharmacol Exp Ther (w/Suppl. Matl.), 344(3):655-664 (Mar. 1, 2013).
Pei, Y, et al., "Regioselective syntheses of 3-aminomethyl-5-substituted isoxazoles: A facile and chemoselective reduction of azide to amine by sodium borohydride using 1,3-propanedithiol as a catalyst" Tetrahedron Lett 34(47):7509-7512 (Nov. 19, 1993).
The Cancer Genome Atlas Network et al., "Genomic Classification of Cutaneous Melanoma" Cell 161(7):1681-1696 (Jun. 18, 2015).
Wang, J., et al., "P-glycoprotein (MDR1/ABCB1) and Breast Cancer Resistance Protein (BCRP/ABCG2) affect brain accumulation and intestinal disposition of encorafenib in mice" Pharmacol Res 129:414-423 (Mar. 1, 2018).
Weeraratna, A., "RAF around the Edges—The Paradox of BRAF Inhibitors" N Engl J Med 366(3):271-273 (Jan. 19, 2012).
Wenglowsky, S., et al., "Highly potent and selective 3-N-methylquinazoline-4(3H)-one based inhibitors of B-Raf(V600E) kinase" Bioorg Med Chem Lett 24(8):1923-1927 (Apr. 15, 2014).
"International Preliminary Report on Patentability—PCT/EP2021/086049" (Report Issuance Date: Jun. 13, 2023; Chapter I),:pp. 1-8 (Jun. 29, 2023).
"International Preliminary Report on Patentability—PCT/EP2021/086050" (Report Issuance Date: Jun. 13, 2023; Chapter I),:pp. 1-8 (Jun. 29, 2023).
"International Search Report—PCT/EP2021/086049" (w/Written Opinion),:pp. 1-11 (Mar. 14, 2022).
"International Search Report—PCT/EP2021/086050" (w/Written Opinion),:pp. 1-15 (Mar. 14, 2022).
Maillard, J. et al., "Derivatives of 3(H) quinazolinone-4 endowed with anti-inflammatory properties" Chimica Therapeutica (English-language summary on p. 238), 2(4):231-239 ( 1967).
Pokrovsky, V.I. et al. Popular Medical Encyclopaedia Pokrovsky, V.I., & Rams Academician, eds., 4th edition, Ulyanovsk, RU:Bookworm,:317 ( 1997).
Pokrovsky, V.I. et al. Small Medical Encyclopedia, Kidney Stone Disease—Substance Abuse, Meditsina (Medicine) (English translation with Russian language version attached), Moscow, RU: vol. 5:90-96 ( 1996).
Ren, L., et al., "The discovery of potent and selective pyridopyrimidin-7-one based inhibitors of B-RafV600E kinase" Bioorg Med Chem Lett 22(10):3387-3391 (May 15, 2012).
Wang, X., et al., "Conformation-Specific Effects of Raf Kinase Inhibitors—Miniperspective" ACS J Med Chem 55(17):7332-7341 (Jul. 18, 2012).
Zhang, C. et al., "RAF inhibitors that evade paradoxical MAPK pathway activation" Nature 526:583 (Oct. 22, 2015).

\* cited by examiner

A375 inhibition - Example 1

A375 inhibition - Example 2

A375 inhibition - Example AR-25

HCT-116 activation; Example 1 = ERN; max. activation of paradox inducer Dabrafenib is set to 100%; PLX8394 is a positive control for a paradox breaker HCT-116 activation; Example 2 = ERN; max. activation of paradox inducer Dabrafenib is set to 100%; PLX8394 is a positive control for a paradox breaker HCT-116 activation; AR-25 = ERN; max. activation of paradox inducer Dabrafenib is set to 100%; PLX8394 is a positive control for a paradox breaker

FIG. 7

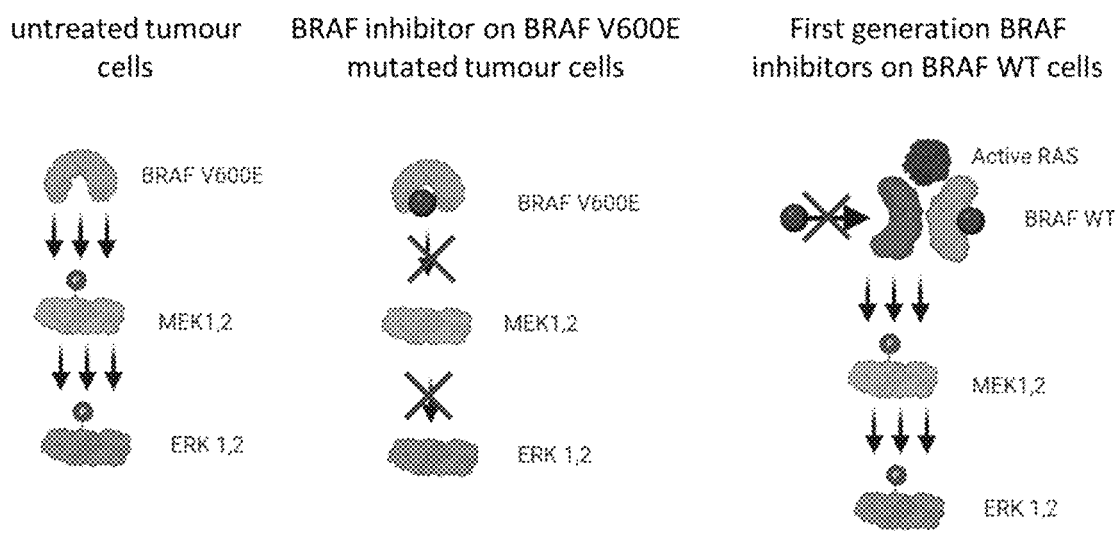

First generation BRAF inhibitors induce paradoxical activation of the MAP kinase signaling pathway in BRAF WT cells

Left: BRAF is part of the first node of the MAP kinase signalling pathway and mutant BRAF is an oncogenic driver.

Center: In BRAF V600E/K mutated tumors BRAF signals as monomer, a condition in which the protein is inhibited by first generation BRAF inhibitors.

Right: First generation BRAF inhibitors promote BRAF WT homo and/or hetero dimerization. In this context the protomer non occupied by the BRAF inhibitor acquires a conformation unfavourable for inhibitor binding. The outcome of the treatment with a first generation BRAF inhibitor, in this context, is paradoxically increased MAPK activation and consequent tumor growth in BRAF WT cells.

Compound Example 1 triggered dose dependent antitumor activity starting from 1 mg/kg daily evidencing potent brain-permeability mediated efficacy

METHYLQUINAZOLINONE DERIVATIVES

CROSS-REFERENCE TO RELATED APPLICATIONS

This application is a continuation of International Application No. PCT/EP2020/084976, filed Dec. 8, 2020, which claims priority to EP Application No. 19214941.7, filed Dec. 10, 2019, the disclosures of which are incorporated herein by reference in their entireties.

The present invention provides a new compound, its manufacture, pharmaceutical compositions containing it and its use as therapeutically active substance. The compound of the invention that is a BRAF inhibitor and has paradox breaking properties.

The present invention provides in particular a novel compound of formula (I)

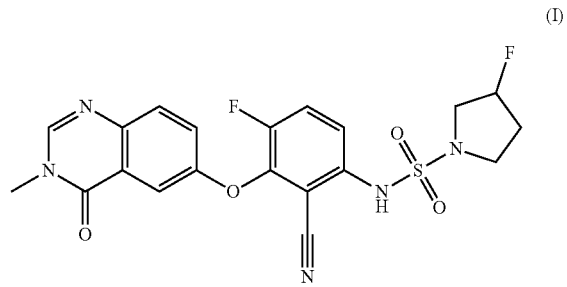 [SMILES: Cn1cnc2ccc(Oc3c(F)ccc(NS(=O)(=O)N4CCC(F)C4)c3C#N)cc2c1=O]

or a pharmaceutically acceptable salt thereof.

The Rapidly Accelerated Fibrosarcoma (RAF) class of serine-threonine kinases comprise three members (ARAF, BRAF, RAF1) that compose the first node of the MAP kinase signalling pathway. Despite the apparent redundancy of the three RAF isoforms in signalling propagation through phosphorylation of MEK1 and 2, frequent oncogenic activating mutations are commonly found only for BRAF. In particular, substitution of V600 with glutamic acid or lysine renders the kinase highly activated with consequent hyperstimulation of the MAPK pathway, independently from external stimulations (Cell. 2015 Jun. 18; 161(7): 1681-1696).

Mutant BRAF is a targetable oncogenic driver and three BRAF inhibitors (vemurafenib, dabrafenib and encorafenib) reached the market up to now showing efficacy in BRAFV600E-positive melanoma. However rapid acquisition of drug resistance is almost universally observed and the duration of the therapeutic benefits for the targeted therapy remains limited.

Moreover, the developed BRAF inhibitors revealed an unexpected and "paradoxical" ability to repress MAPK signalling in BRAFV600E-driven tumours while the same inhibitors presented MAPK stimulatory activities in BRAF wild type (WT) models (N Engl J Med 2012; 366:271-273; and British Journal of Cancer volume 111, pages 640-645 (2014)).

Mechanistic studies on the RAF paradox then clarified that oncogenic BRAFV600E phosphorylates MEK 1/2 in its monomeric cytosolic form while WT BRAF and RAF1 activation requires a complex step of events including cell membrane translocation and homo and/or heterodimerization promoted by activated RAS (KRAS, NRAS, HRAS) (Nature Reviews Cancer volume 14, pages 455-467(2014)).

The binding of inhibitors like vemurafenib, dabrafenib or encorafenib to a WT BRAF or RAF1 protomer, quickly induces RAF homo and/or hetero dimerization and membrane association of the newly formed RAF dimer. In the dimeric conformation, one RAF protomer allosterically induces conformational changes of the second resulting in a kinase active status and, importantly, in a conformation unfavourable for the binding of the inhibitor. The dimer induced by drug treatment, as a result, promotes MEK phosphorylation by the catalysis operated by the unbound protomer with hyperactivation of the pathway.

The RAF paradox results in two clinically relevant consequences: 1) accelerated growth of secondary tumours upon BRAFi monotherapy (mainly keratochantoma and squamous-cell carcinomas) (N Engl J Med 2012; 366:271-273) and 2) the acquisition of drug resistance in the setting of BRAFi monotherapy as well as in combinations of BRAFi+MEKi presents activation of dimer-mediated RAF signalling by genetically driven events including RAS mutations, BRAF amplifications, expression of dimeric-acting BRAF splice variants (Nature Reviews Cancer volume 14, pages 455-467(2014)). There is thus the need for RAF inhibitors capable of breaking that paradox.

Furthermore, the currently approved classical BRAF inhibitors Vemurafenib (Mol. Pharmaceutics 2012, 9, 11, 3236-3245), Dabrafenib (J Pharmacol Ex Ther 2013, 344 (3) 655-664) and Encorafenib (Pharmacol Res. 2018; 129:414-423) all have very poor brain permeability. This is major limitation for the use of those classical BRAF inhibitors for the treatment of brain cancer or brain metastases. There is thus the need for BRAF inhibitors having improved brain permeability.

The present invention relates to the surprising finding, that the BRAF inhibitor of formula (I) is a more potent and selective BRAF inhibitor showing considerably less paradoxial activation of the MAPK signaling pathway while retaining high potency. This compound can thus be referred to as a paradox breaker or RAF paradox breaker, in contrast to compounds inducing the RAF paradox (and which could be referred to as paradox inducers or RAF paradox inducers). In addition to being a paradox breaker, the compound of formula (I) also has very potent brain penetration properties, thus providing an urgently needed alternative therapy for the treatment of cancers in the brain.

BRIEF DESCRIPTION OF THE FIGURES

FIG. 7 depicts the paradoxical activation of the MAP kinase pathway induced by first generation BRAF inhibitors. BRAF is part of the first node of the MAP kinase signalling pathway and mutant BRAF is an oncogenic driver (left). In BRAF V600E/K mutated tumors BRAF signals as monomer, a condition in which the protein is inhibited by first generation BRAF inhibitors (middle). First generation BRAF inhibitors promote BRAF WT homo and/or hetero dimerization (top, right). In this context the protomer non occupied by the BRAF inhibitor acquires a conformation unfavourable for inhibitor binding (middle, right). The outcome of the treatment with a first generation BRAF inhibitor, in this context, is paradoxically increased MAPK activation and consequent tumor growth in BRAF WT cells (bottom, right).

Figure 1:
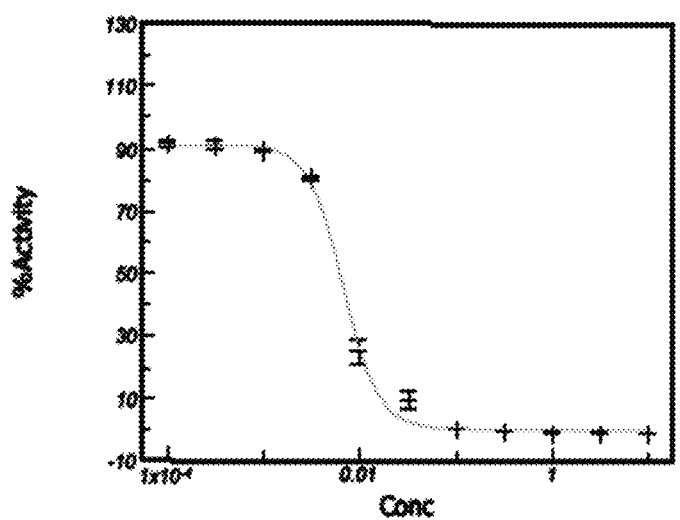
FIG. 1 discloses the P-ERK inhibition curve induced by example 1 in the BRAF mutant cell line A375.

WO2012/118492 discloses references compounds AR-25 as example 25, AR-30 as example 30 and AR-31 as example 31.

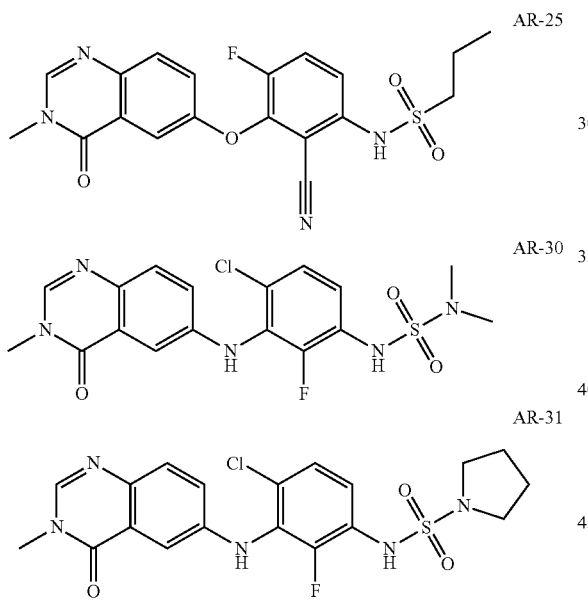

The term "pharmaceutically acceptable salt" refers to those salts of the compound of formula (I) which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, in particular hydrochloric acid, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein and the like. In addition, these salts may be prepared by addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyimine resins and the like. Particular pharmaceutically acceptable salts of compound of formula (I) are the hydrochloride salts, methanesulfonic acid salts and citric acid salts.

The compound of formula (I) contains one asymmetric center and can be present in the form of optically pure enantiomers or mixtures of enantiomers such as, for example, racemates.

According to the Cahn-Ingold-Prelog Convention the asymmetric carbon atom can be of the "R" or "S" configuration.

Also an embodiment of the present invention is the compound according to formula (I) as described herein or a pharmaceutically acceptable salt thereof, in particular the compound according to formula (I) as described herein, more particularly the compound of formula (Ia) or (Ib) as described herein.

The invention also relates to a pharmaceutically acceptable salt of the compound of formula (I), and wherein the pharmaceutically acceptable salt can be selected from hydrochloride salts, methanesulfonic acid salts and citric acid salts.

Also an embodiment of the present invention is the compound according to formula (Ia).

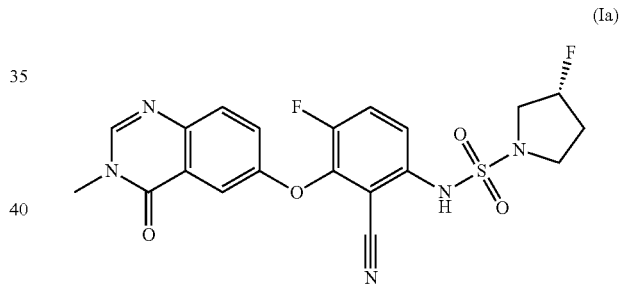

Also an embodiment of the present invention is the compound according to formula (Ib).

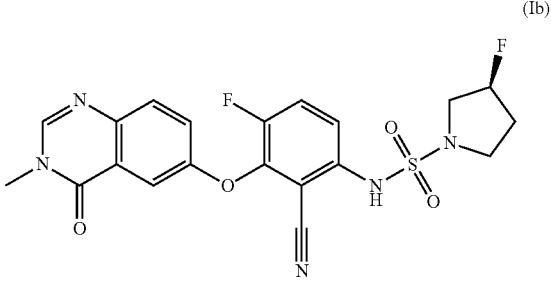 [SMILES: Cn1cnc2ccc(Oc3c(F)ccc(NS(=O)(=O)N4CC[C@H](F)C4)c3C#N)cc2c1=O]

Processes for the manufacture of the compounds of formula (Ia) and (Ib) as described herein are also an object of the invention.

The preparation of the compound of formula (I) of the present invention may be carried out in sequential or convergent synthetic routes. Syntheses of the invention are shown in the following general scheme. The skills required for carrying out the reactions and purifications of the resulting products are known to those skilled in the art.

In more detail, the compound of formula (I) can be manufactured by the methods given below, by the methods given in the examples or by analogous methods. Appropriate reaction conditions for the individual reaction steps are known to a person skilled in the art. The reaction sequence is not limited to the one displayed in scheme 1, however, depending on the starting materials and their respective reactivity the sequence of reaction steps can be freely altered. Starting materials are either commercially available or can be prepared by methods analogous to the methods given below, by methods described in references cited in the description or in the examples, or by methods known in the art.

Scheme 1

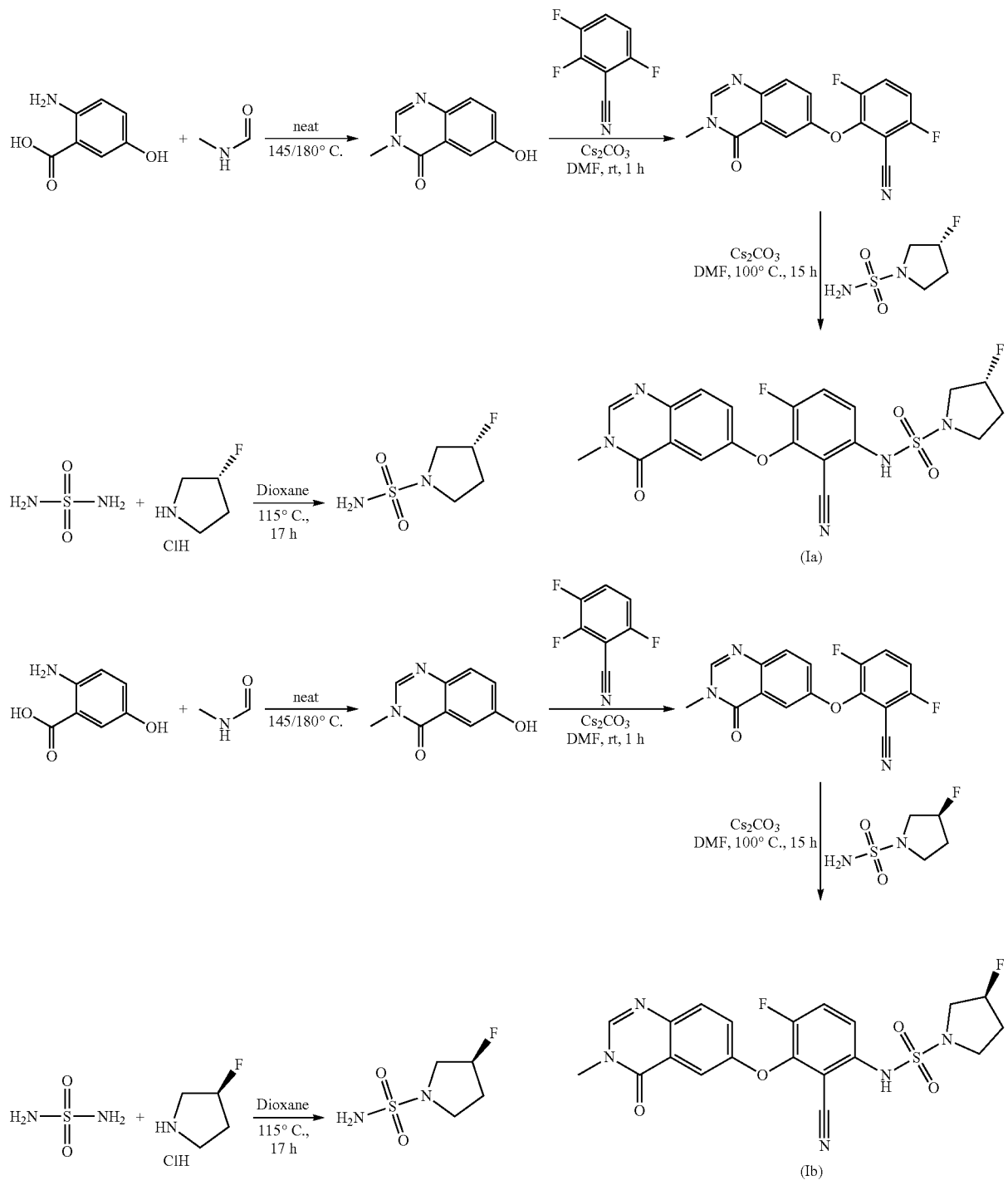

It will be appreciated that the compound of formula (I) in this invention may be derivatised at functional groups to provide derivatives which are capable of conversion back to the parent compound in vivo.

The invention thus also relates to a process for the preparation of a compound according to the invention, comprising the reaction of a compound of formula (B1)

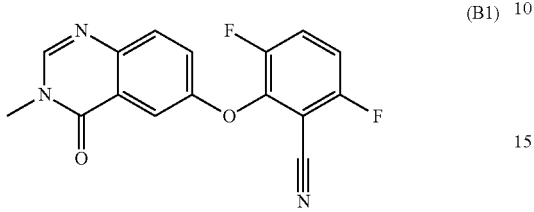

with a compound of formula (B2)

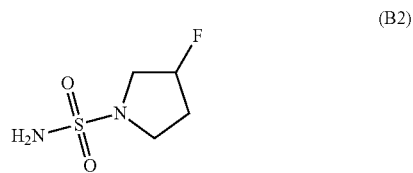

in the presence of a base.

The reaction can conveniently be carried out in a solvent. The solvent can be for example DMF.

The reaction can conveniently be carried out in presence of a base. The base can be for example cesium carbonate.

Convenient conditions for the reaction can be between around 30° C. and around 150° C., particularly between around 50° C. and around 130° C., more particularly between around 70° C. and around 120° C. Convenient conditions are around 100° C. for between around 1 h and around 48 hrs, in particular between around 2 hrs and around 20 hrs.

The invention also relates to a compound according to the invention when manufactured according to a process of the invention.

The invention also relates in particular to:
A compound of formula (I) as described herein, or a pharmaceutically acceptable salt thereof, for use as therapeutically active substance;
A pharmaceutical composition comprising a compound of formula (I) as described herein, or a pharmaceutically acceptable salt thereof, and a therapeutically inert carrier;
A compound of formula (I) as described herein, or a pharmaceutically acceptable salt thereof, for use in the treatment or prophylaxis of cancer;
A compound of formula (I) as described herein, or a pharmaceutically acceptable salt thereof, for use in the treatment or prophylaxis of thyroid cancer, colorectal cancer, brain cancer, melanoma or non-small cell lung cancer (NSCLC);
The use of a compound of formula (I) as described herein, or a pharmaceutically acceptable salt thereof, for the treatment or prophylaxis of thyroid cancer, colorectal cancer, brain cancer, melanoma or NSCLC;
The use of a compound of formula (I) as described herein, or a pharmaceutically acceptable salt thereof, for the preparation of a medicament for the treatment or prophylaxis of thyroid cancer, colorectal cancer, brain cancer, melanoma or NSCLC;
A method for the treatment of cancer, which method comprises administering an effective amount of a compound of formula (I) as described herein, or a pharmaceutically acceptable salt thereof, to a patient in need thereof; and
A method for the treatment or prophylaxis of thyroid cancer, colorectal cancer, brain cancer, melanoma or NSCLC, which method comprises administering an effective amount of a compound of formula (I) as described herein, or a pharmaceutically acceptable salt thereof, to a patient in need thereof.

A certain embodiment of the invention relates to the compound of formula (I) as described herein, or a pharmaceutically acceptable salt thereof, for use in the therapeutic and/or prophylactic treatment of cancer, in particular BRAF mutant driven cancer, more particularly thyroid cancer, colorectal cancer, brain cancer, melanoma or NSCLC.

A certain embodiment of the invention relates to the compound of formula (I) as described herein, or a pharmaceutically acceptable salt thereof, for the manufacture of a medicament for the therapeutic and/or prophylactic treatment of cancer, in particular BRAF mutant driven cancer, more particularly thyroid cancer, colorectal cancer, brain cancer, melanoma or NSCLC.

A certain embodiment of the invention relates to a pharmaceutical composition comprising the compound of formula (I) as described herein, or a pharmaceutically acceptable salt thereof, and a pharmaceutically acceptable excipient.

A certain embodiment of the invention relates to a method for the therapeutic and/or prophylactic treatment of cancer, in particular BRAF mutant driven cancer, more particularly thyroid cancer, colorectal cancer, brain cancer, melanoma or non-small cell lung cancer (NSCLC) by administering an effective amount of the compound of formula (I) as described herein, or a pharmaceutically acceptable salt thereof, to a patient in need thereof.

A certain embodiment of the invention relates to the compound of formula (I) as described herein, or a pharmaceutically acceptable salt thereof, for the use as a medicament in therapeutic and/or prophylactic treatment of a patient with BRAF mutant driven cancers, in particular thyroid cancer, colorectal cancer, brain cancer, melanoma or NSCLC, comprising determining the BRAF mutation status in said patient and then administering the compound of formula (I) as described herein, or a pharmaceutically acceptable salt thereof, to said patient.

A certain embodiment of the invention relates to the compound of formula (I) as described herein, or a pharmaceutically acceptable salt thereof, for the use as a medicament in therapeutic and/or prophylactic treatment of brain metastases.

Furthermore, the invention includes all substituents in their corresponding deuterated form, wherever applicable, of the compound of formula (I).

Furthermore, the invention includes all substituents in their corresponding tritiated form, wherever applicable, of the compound of formula (I).

A certain embodiment of the invention relates to the compound of formula (I) as described herein, or a pharmaceutically acceptable salt thereof, wherein at least one substituent comprises at least one radioisotope. Particular examples of radioisotopes are $^2$H, $^3$H, $^{13}$C, $^{14}$C and $^{18}$F.

Furthermore, the invention includes all optical isomers, i.e. diastereoisomers, diastereomeric mixtures, racemic mixtures, all their corresponding enantiomers and/or tautomers as well as their solvates, wherever applicable, of the compound of formula (I).

If desired, racemic mixtures of the compound of the invention may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography.

In the embodiments, where an optically pure enantiomer is provided, optically pure enantiomer means that the compound contains >90% of the desired isomer by weight, particularly >95% of the desired isomer by weight, or more particularly >99% of the desired isomer by weight, said weight percent based upon the total weight of the isomer of the compound. A chirally pure or chirally enriched compound may be prepared by chirally selective synthesis or by separation of enantiomers. The separation of enantiomers may be carried out on the final product or alternatively on a suitable intermediate.

Another embodiment of the invention provides a pharmaceutical composition or medicament containing a compound of the invention and a therapeutically inert carrier, diluent or excipient, as well as a method of using the compounds of the invention to prepare such composition and medicament. In one example, the compound of formula (I) may be formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends mainly on the particular use and the concentration of compound, but preferably ranges anywhere from about 3 to about 8. In one example, a compound of formula (I) is formulated in an acetate buffer, at pH 5. In another embodiment, the compound of formula (I) is sterile. The compound may be stored, for example, as a solid or amorphous composition, as a lyophilized formulation or as an aqueous solution.

Compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners.

Also an embodiment of the present invention is the compound of formula (I) as described herein, when manufactured according to any one of the described processes.

Assay Procedures

Materials

DMEM no-phenol red medium supplemented with L-glutamine was purchased from (Thermo Fisher Scientific). Fetal bovine serum (FBS) was purchased from VWR. Advanced ERK phospho-T202/Y204 kit—10,000 tests was purchased from Cisbio cat #64AERPEH. A375 and HCT116 cells were originally obtained from ATCC and banked by the Roche repository. 384-well microplates were purchased from Greiner Bio-One, 384-well, (With Lid, HiBase, Low volume cat 784-080).

HTRF Assay for P-ERK Determination in A375 or HCT116 Cells

A375 is a cellular cancer model expressing V600E mutated BRAF and HCT116 a cellular cancer model expressing WT BRAF. First generation BRAF inhibitors such as e.g. dabrafenib induce a paradox effect on tumour cells in that they inhibit the growth of V600E mutated BRAF cells (such as e.g. A375), while they activate growth in WT BRAF cells (such as e.g. HCT 116). ERK 1,2 phosphorylation (terminal member of the phosphorylation cascade of the MAPK pathway) is hereafter reported as main readout for the activation status of the MAPK pathway. Prior to the assay, A375 and HCT116 cell lines are maintained in DMEM no-phenol red medium supplemented with 10% fetal bovine serum (FBS). Following compound treatment, P-ERK levels are determined by measuring FRET fluorescence signal induced by selective binding of 2 antibodies provided in the mentioned kit (Cisbio cat #64AERPEH) on ERK protein when phosphorylated at Thr202/Tyr204. Briefly, 8000 cells/well in 12 μl media/well are plated in the 384-well plate and left overnight in the incubator (at 37° C. with 5% CO2-humidified atmosphere), the following day the plate is treated in duplicate with test compounds, dabrafenib and PLX8394 (the latter two as controls) at the following final drug concentrations: 10 μM-3 μM-1 μM-0.3 μM-0.10 μM-0.030 μM-0.01 μM-0.003 μM-0.001 μM, all wells are subjected to DMSO normalization and drug incubation occurs for 1 hour. Then, 4 μl of a 4× lysis buffer supplied with the kit are added to the wells, the plate is then centrifuged for 30 second (300 rcf) and incubated on a plate shaker for 1 h at RT.

At the end of the incubation 4 μL/well of advanced P-ERK antibody solution (prepared according to manufacturer's instruction) followed by 4 μL/well of criptate P-ERK antibody solution (prepared according to manufacturer's instruction) (Cisbio cat #64AERPEH) are added to test wells.

In order to allow proper data normalization control wells non drug treated reported in the following table are always included in each plate (according to manufacturer's instruction):

p-ERK HTRF Well Compositions (μl):

| neg ctrl | pos ctrl | neut ctrl | cpd | blank | |
|---|---|---|---|---|---|
| — | — | 12 | 12 | 12 | Cells |
| 12 | — | — | — | — | Media |
| — | — | — | <0.05 | — | Cpd |
| — | 16 | — | — | — | control lysate (ready-to-use) |
| 4 | — | 4 | 4 | 4 | 4× lysis buffer |
| 4 | 4 | 4 | 4 | — | Advanced p-ERK antibody solution |
| — | — | — | — | 4 | Advanced p-ERK1/2 Cryptate antibody solut. |
| 20 | 20 | 20 | 20 | 20 | Total volume in Well |

The plate is then centrifuged at 300 rcf for 30 second, sealed to prevent evaporation and incubated overnight in the dark at room temperature.

The plate is then analyzed and fluorescence emission value collected through a Pherastast FSX (BMG Labtech) apparatus at 665 and 620 nM.

The obtained fluorescence values are processed according to the formula Ratio=Signal(620 nm)/Signal(625 nm)*10000 then the average of the ratio on the blank is subtracted to all values.

Figure 2:
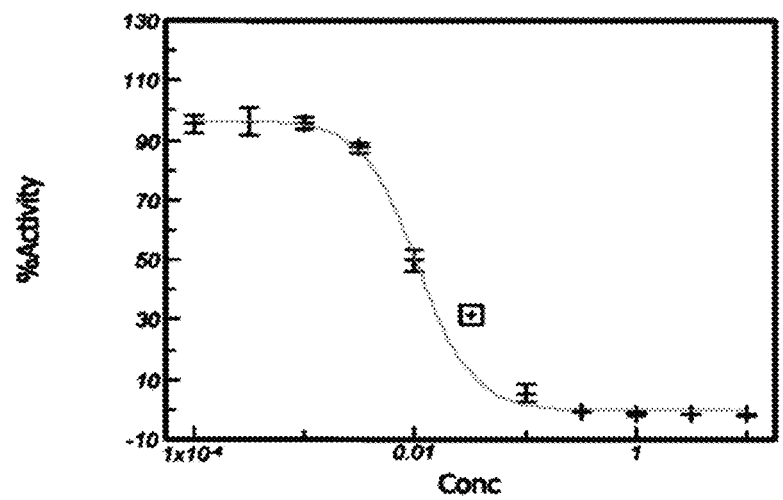
FIG. 2 discloses the P-ERK inhibition curve induced by example 2 in the BRAF mutant cell line A375.
Figure 3:
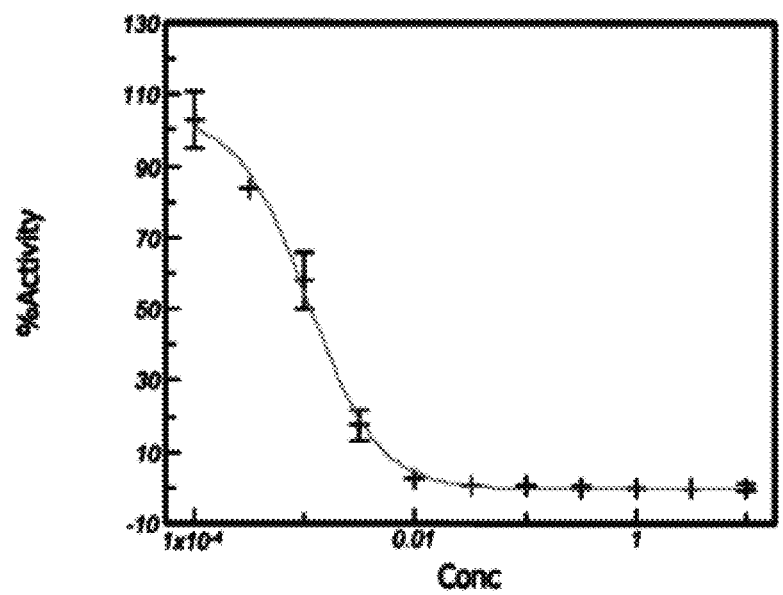
FIG. 3 discloses the P-ERK inhibition curve induced by reference compound AR-25 in the BRAF mutant cell line A375.

Data are normalized in the case of A375 cells (BRAF inhibition) considering the average of the ratio (blank subtracted) derived by DMSO only treated cells as 100% and by considering the average of the ratio (blank subtracted) derived by 10 µM dabrafenib treated cells as 0%. Mean of the normalized points are fitted with sigmoidal curve and IC50 determined. The results are shown in Tables 1-2 and FIG. 1-FIG. 3.

Figure 4:
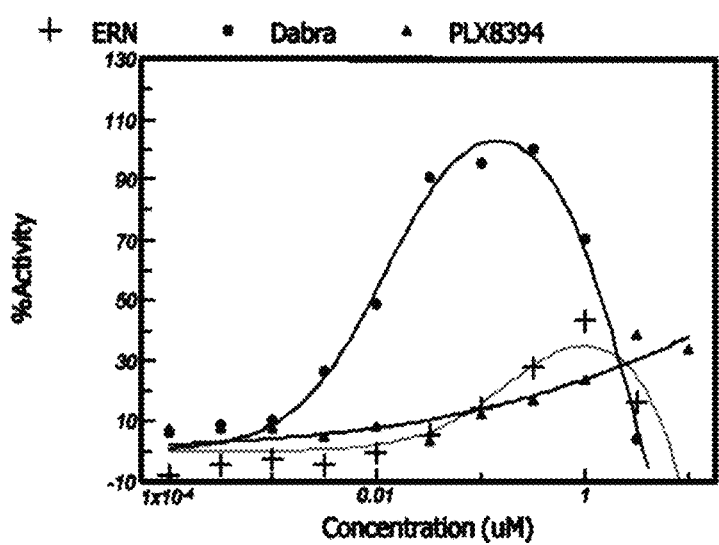
FIG. 4 discloses the P-ERK activation curve induced by example 1 in the WT BRAF cell line HCT-116. For comparison the data generated by treatment with control compounds dabrafenib (paradox inducer) and PLX-8394 (paradox breaker) is also shown.
Figure 5:
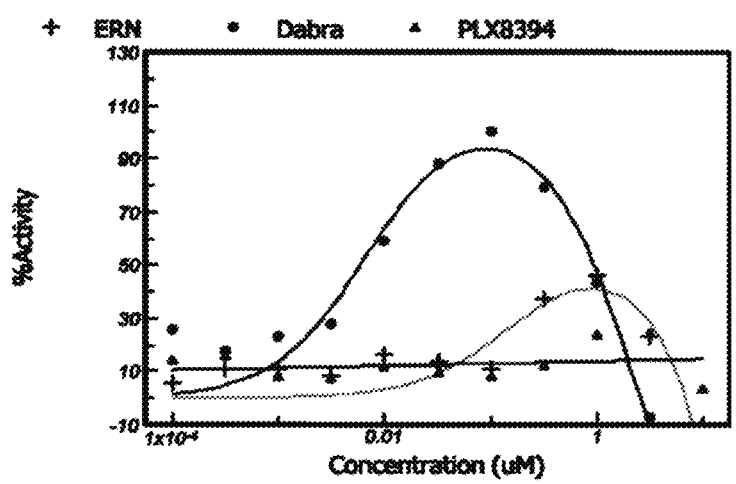
FIG. 5 discloses the P-ERK activation curve induced by example 2 in the WT BRAF cell line HCT-116. For comparison the data generated by treatment with control compounds dabrafenib (paradox inducer) and PLX-8394 (paradox breaker) is also shown.
Figure 6:
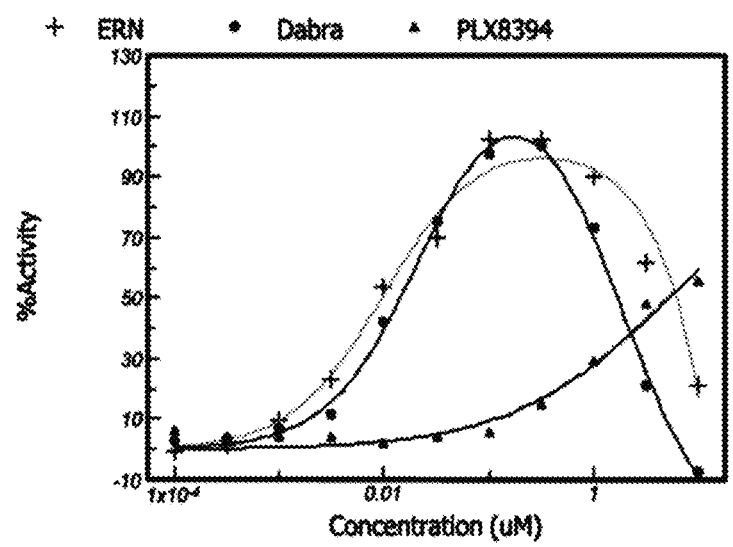
FIG. 6 discloses the P-ERK activation curve induced by reference compound AR-25 in the WT BRAF cell line HCT-116. For comparison the data generated by treatment with control compounds dabrafenib (paradox inducer) and PLX-8394 (paradox breaker) is also shown.

Data are normalized in the case of HCT116 cells (BRAF activation) considering the average of the ratio (blank subtracted) derived by DMSO only treated cells as 0% and by considering the average of the ratio (blank subtracted) derived by dabrafenib treated cells at the concentration which provides the highest signal as 100%. Individual points are fitted with either sigmoidal or bell shape curves, and the percentage of activation compared to maximum dabrafenib-mediated activation is determined. The EC50 is the concentration at which activation equal to 50% of the maximum achieved by dabrafenib is obtained. The results are shown in Tables 2 and FIG. 4-FIG. 6.

In case the activation does not reach 50% of the maximum achieved by dabrafenib, then the EC50 calculation is not applicable.

The Percentage of Maximum paradox inducing effect from dabrafenib is determined by evaluating the percentage at which the test compound induce its maximum P-ERK signal as percentage of the highest signal produced by dabrafenib within the dose range tested.

TABLE 1

Example 1 and Example 2 have high affinity for RAF kinases and high selectivity over C-terminal Src kinase (CSK) and lymphocyte-specific tyrosine protein kinase (LCK), when compared to AR-30 and AR-31.

| | Kd (µM) | | | | |
|---|---|---|---|---|---|
| Ex. | BRAF | BRAF V600E | CRAF | CSK | LCK |
| 1 | 0.0006 | 0.0012 | 0.0017 | 23.3 | 40 |
| 2 | 0.0013 | 0.0009 | 0.0012 | 9.16 | 20.12 |
| AR-25 | 0.0001 | 0.0002 | 0.0003 | >40 | >40 |
| AR-30 | 0.1740 | 0.5040 | 0.8220 | 8.007 | 10.352 |
| AR-31 | 0.0459 | 0.1190 | 0.1903 | 1.208 | 11.975 |

TABLE 2

Example 1 and Example 2 are breaking the paradoxical RAF activation in HCT-116 cancer cells expressing WT BRAF. When compared with dabrafenib or with AR-25 the maximum paradox inducing effect is reduced to less than 50%.

| Ex. | pERK IC$_{50}$ (nM) A375 | p-ERK EC50 (nM) conc. (nM) at which the compound induces P-ERK activation of 50% of that induced by dabrafenib (Positive control paradox inducer) HCT-116 | Percentage of Maximum paradox inducing effect from dabrafenib |
|---|---|---|---|
| 1 | 6.9 | not applicable | 43.65% |
| 2 | 10.6 | not applicable | 46.2% |
| AR-25 | 1.1 | 9.6 | 103% |
| AR-30 | 406 | >1000 | 59% |
| AR-31 | 311 | >1000 | 51.2% |

CSF $K_{p,uu}$ Measurement for Assessing Brain Penetration Potential

The CSF $K_{p,uu}$ is the ratio of the concentration in cerebrospinal fluid (CSF):unbound plasma exposure and $K_{p,uu}$ values ≥1 indicate good brain penetration. For compound Example 1, single oral dose studies in mouse and rat, sequential plasma and CSF concentrations (up to 24 h post dose) were measured by LC-MS/MS to calculate the CSF $K_{p,uu}$. For multiple oral dose studies in rat and minipig the plasma and CSF concentrations approximating Tmax (3 h post last dose) were measured by LC-MS/MS and used to calculate the CSF $K_{p,uu}$.

TABLE 3

Physicochemical and ADME properties of compound Example 1. CSF $K_{p,uu}$ values ≥ 1 indicate good brain penetration for Example 1. In addition, the temporal relationship of plasma and CSF was assessed up to 24 h post dose in the single dose rat pharmacokinetic (PK) study and indicated fast and extensive distribution into CSF.

| | Value | Class |
|---|---|---|
| Molecular weight/polar surface aera | 461/99 | — |
| BCS (biopharmaceutics classific. system) | — | 2 |
| *P-gp Apical Efflux ratio | 1.5 | Low |
| Plasma protein binding (%) (mouse, rat, minipig, monkey, human) | ≥99 | Very high |
| Mouse CSF $K_{p,uu}$ Single oral dose 10 mg/kg | ≥1 | High |
| Rat CSF $K_{p,uu}$ Single oral dose 20 mg/kg | ≥1 | High |
| Rat CSF $K_{p,uu}$ Multiple oral dosing @ 300 mg/kg/day (2-week DRF) | ≥1 | High |
| Minipig CSF $K_{p,uu}$ Multiple oral dosing @ 300 mg/kg/day (2-week DRF) | ≥1 | High |

Figure 8:
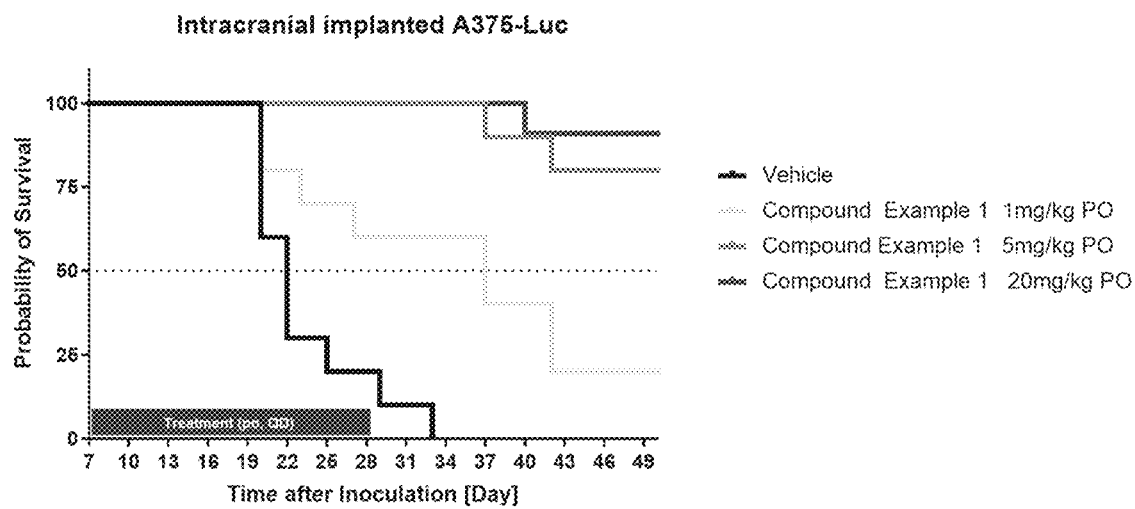
FIG. 8 discloses that compound Example 1 triggered dose dependent antitumor activity starting from 1 mg/kg daily evidencing potent brain-permeability mediated efficacy.

*LLC-PK1 cell line transfected with MDR1, assessed in presence/absence of P-gp inhibitor Intracranial Implanted A375-Luc A375 BRAF V600E cancer cells constitutively expressing luciferase were injected intracranially in immunocompromised mice. Treatment with compound Example 1 was initiated at day 7 from the intracranial injection and continued for 2 weeks. The different groups were subject to daily oral administration of 1 mg/kg, 5 mg/kg and 20 mg/kg of Example 1 respectively. The results are shown in FIG. 8.

The compound of formula (I) or a pharmaceutically acceptable salt thereof can be used as a medicament (e.g. in the form of a pharmaceutical preparation). The pharmaceutical preparation can be administered internally, such as orally (e.g. in the form of tablets, coated tablets, dragées, hard and soft gelatin capsules, solutions, emulsions or suspensions), nasally (e.g. in the form of nasal sprays), rectally (e.g. in the form of suppositories) or topical ocularly (e.g. in the form of solutions, ointments, gels or water soluble polymeric inserts). However, the administration can also be effected parenterally, such as intramuscularly, intravenously, or intraocularly (e.g. in the form of sterile injection solutions).

The compound of formula (I) or a pharmaceutically acceptable salt thereof can be processed with pharmaceutically inert, inorganic or organic adjuvants for the production of tablets, coated tablets, dragees, hard gelatin capsules, injection solutions or topical formulations Lactose, corn starch or derivatives thereof, talc, stearic acid or its salts etc. can be used, for example, as such adjuvants for tablets, dragées and hard gelatin capsules.

Suitable adjuvants for soft gelatin capsules, are, for example, vegetable oils, waxes, fats, semi-solid substances and liquid polyols, etc.

Suitable adjuvants for the production of solutions and syrups are, for example, water, polyols, saccharose, invert sugar, glucose, etc.

Suitable adjuvants for injection solutions are, for example, water, alcohols, polyols, glycerol, vegetable oils, etc.

Suitable adjuvants for suppositories are, for example, natural or hardened oils, waxes, fats, semi-solid or liquid polyols, etc.

Suitable adjuvants for topical ocular formulations are, for example, cyclodextrins, mannitol or many other carriers and excipients known in the art.

Moreover, the pharmaceutical preparations can contain preservatives, solubilizers, viscosity-increasing substances, stabilizers, wetting agents, emulsifiers, sweeteners, colorants, flavorants, salts for varying the osmotic pressure, buffers, masking agents or antioxidants. They can also contain still other therapeutically valuable substances.

The dosage can vary in wide limits and will, of course, be fitted to the individual requirements in each particular case. In general, in the case of oral administration a daily dosage of about 0.1 mg to 20 mg per kg body weight, preferably about 0.5 mg to 4 mg per kg body weight (e.g. about 300 mg per person), divided into preferably 1-3 individual doses, which can consist, for example, of the same amounts, should it be appropriate. In the case of topical administration, the formulation can contain 0.001% to 15% by weight of medicament and the required dose, which can be between 0.1 and 25 mg in can be administered either by single dose per day or per week, or by multiple doses (2 to 4) per day, or by multiple doses per week It will, however, be clear that the upper or lower limit given herein can be exceeded when this is shown to be indicated.

Pharmaceutical Compositions

The compound of formula (I) or a pharmaceutically acceptable salt thereof can be used as therapeutically active substance, e.g. in the form of a pharmaceutical preparation. The pharmaceutical preparation can be administered orally, e.g. in the form of tablets, coated tablets, dragees, hard and soft gelatin capsules, solutions, emulsions or suspensions. The administration can, however, also be effected rectally, e.g. in the form of suppositories, or parenterally, e.g. in the form of injection solutions.

The compound of formula (I) and the pharmaceutically acceptable salts thereof can be processed with a pharmaceutically inert, inorganic or organic carriers for the production of a pharmaceutical preparation. Lactose, corn starch or derivatives thereof, talc, stearic acids or its salts and the like can be used, for example, as such carriers for tablets, coated tablets, dragees and hard gelatin capsules. Suitable carriers for soft gelatin capsules are, for example, vegetable oils, waxes, fats, semi-solid and liquid polyols and the like. Depending on the nature of the active substance no carriers are however usually required in the case of soft gelatin capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical preparation can, moreover, contain pharmaceutically acceptable auxiliary substances such as preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

Medicaments containing the compound of formula (I) or a pharmaceutically acceptable salt thereof and a therapeutically inert carrier are also provided by the present invention, as is a process for their production, which comprises bringing one or more compounds of formula (I) and/or pharmaceutically acceptable salts thereof and, if desired, one or more other therapeutically valuable substances into a galenical administration form together with one or more therapeutically inert carriers.

The dosage can vary within wide limits and will, of course, have to be adjusted to the individual requirements in each particular case. In the case of oral administration the dosage for adults can vary from about 0.01 mg to about 1000 mg per day of a compound of general formula (I) or of the corresponding amount of a pharmaceutically acceptable salt thereof. The daily dosage may be administered as single dose or in divided doses and, in addition, the upper limit can also be exceeded when this is found to be indicated.

The following examples illustrate the present invention without limiting it, but serve merely as representative thereof. The pharmaceutical preparations conveniently contain about 1-500 mg, particularly 1-100 mg, of a compound of formula (I). Examples of compositions according to the invention are:

Example A

Tablets of the following composition are manufactured in the usual manner:

TABLE 4 possible tablet composition

| ingredient | mg/tablet | | | |
|---|---|---|---|---|
| | 5 | 25 | 100 | 500 |
| Compound of formula (I) | 5 | 25 | 100 | 500 |
| Lactose Anhydrous DTG | 125 | 105 | 30 | 150 |
| Sta-Rx 1500 | 6 | 6 | 6 | 60 |
| Microcrystalline Cellulose | 30 | 30 | 30 | 450 |
| Magnesium Stearate | 1 | 1 | 1 | 1 |
| Total | 167 | 167 | 167 | 831 |

Manufacturing Procedure
1. Mix ingredients 1, 2, 3 and 4 and granulate with purified water.
2. Dry the granules at 50° C.
3. Pass the granules through suitable milling equipment.
4. Add ingredient 5 and mix for three minutes; compress on a suitable press.

Example B-1

Capsules of the following composition are manufactured:

TABLE 5 possible capsule ingredient composition

| ingredient | mg/capsule | | | |
|---|---|---|---|---|
| | 5 | 25 | 100 | 500 |
| Compound of formula (I) | 5 | 25 | 100 | 500 |
| Hydrous Lactose | 159 | 123 | 148 | — |
| Corn Starch | 25 | 35 | 40 | 70 |
| Talk | 10 | 15 | 10 | 25 |
| Magnesium Stearate | 1 | 2 | 2 | 5 |
| Total | 200 | 200 | 300 | 600 |

Manufacturing Procedure
1. Mix ingredients 1, 2 and 3 in a suitable mixer for 30 minutes.
2. Add ingredients 4 and 5 and mix for 3 minutes.
3. Fill into a suitable capsule.

The compound of formula (I), lactose and corn starch are firstly mixed in a mixer and then in a comminuting machine. The mixture is returned to the mixer; the talc is added thereto and mixed thoroughly. The mixture is filled by machine into suitable capsules, e.g. hard gelatin capsules.

Example B-2

Soft Gelatin Capsules of the following composition are manufactured:

TABLE 6 possible soft gelatin capsule ingredient composition

| ingredient | mg/capsule |
| --- | --- |
| Compound of formula (I) | 5 |
| Yellow wax | 8 |
| Hydrogenated Soya bean oil | 8 |
| Partially hydrogenated plant oils | 34 |
| Soya bean oil | 110 |
| Total | 165 |

TABLE 7 possible soft gelatin capsule composition

| ingredient | mg/capsule |
| --- | --- |
| Gelatin | 75 |
| Glycerol 85% | 32 |
| Karion 83 | 8 (dry matter) |
| Titan dioxide | 0.4 |
| Iron oxide yellow | 1.1 |
| Total | 116.5 |

Manufacturing Procedure

The compound of formula (I) is dissolved in a warm melting of the other ingredients and the mixture is filled into soft gelatin capsules of appropriate size. The filled soft gelatin capsules are treated according to the usual procedures.

Example C

Suppositories of the following composition are manufactured:

TABLE 8 possible suppository composition

| ingredient | mg/supp. |
| --- | --- |
| Compound of formula (I) | 15 |
| Suppository mass | 1285 |
| Total | 1300 |

Manufacturing Procedure

The suppository mass is melted in a glass or steel vessel, mixed thoroughly and cooled to 45° C. Thereupon, the finely powdered compound of formula (I) is added thereto and stirred until it has dispersed completely. The mixture is poured into suppository moulds of suitable size, left to cool; the suppositories are then removed from the moulds and packed individually in wax paper or metal foil.

Example D

Injection solutions of the following composition are manufactured:

TABLE 9 possible injection solution composition

| ingredient | mg/injection solution. |
| --- | --- |
| Compound of formula (I) | 3 |
| Polyethylene Glycol 400 | 150 |
| acetic acid | q.s. ad pH 5.0 |
| water for injection solutions | ad 1.0 ml |

Manufacturing Procedure

The compound of formula (I) is dissolved in a mixture of Polyethylene Glycol 400 and water for injection (part). The pH is adjusted to 5.0 by acetic acid. The volume is adjusted to 1.0 ml by addition of the residual amount of water. The solution is filtered, filled into vials using an appropriate overage and sterilized.

Example E

Sachets of the following composition are manufactured:

TABLE 10 possible sachet composition

| ingredient | mg/sachet |
| --- | --- |
| Compound of formula (I) | 50 |
| Lactose, fine powder | 1015 |
| Microcrystalline cellulose (AVICEL PH 102) | 1400 |
| Sodium carboxymethyl cellulose | 14 |
| Polyvinylpyrrolidon K 30 | 10 |
| Magnesium stearate | 10 |
| Flavoring additives | 1 |
| Total | 2500 |

Manufacturing Procedure

The compound of formula (I) is mixed with lactose, microcrystalline cellulose and sodium carboxymethyl cellulose and granulated with a mixture of polyvinylpyrrolidone in water. The granulate is mixed with magnesium stearate and the flavoring additives and filled into sachets.

EXAMPLES

Abbreviations
DCM=dichloromethane; DMF=dimethylformamide; DMSO=diemethyl sulfoxide; DRF=dose range finding; ESI=electrospray ionization; EtOAc=ethyl acetate; LC-MS/MS=liquid chromatography-MS/MS; MeOH=methanol; MS=mass spectrometry; rt=room temperature; P-gp=P-glycoprotein; SFC=supercritical fluid chromatography.

References compounds AR-25, AR-30 and AR-31 were prepared according to the synthesis disclosed in WO2012/118492 in example 25, example 30 and example 31 respectively.

6-hydroxy-3-methyl-quinazolin-4-one

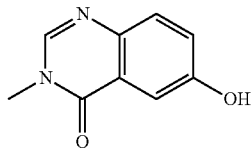

2-Amino-5-hydroxybenzoic acid (10 g, 65.3 mmol, Eq: 1.0) and N-methylformamide (30 g, 29.9 mL, 503 mmol, Eq: 7.7) were heated at 145° C. for 21 h 45 min, then cooled to rt. The reaction mixture was diluted with 50 mL H$_2$O and stirred at rt for 20 min. The resulting precipitate was collected by filtration. The light brown solid was washed 3× with 20 mL water. The solid was taken up in toluene and evaporated to dryness (3×). The solid was dried in vacuo at 40° C. overnight under high vacuum to give the title compound as a light brown solid (10.3 g, 89% yield). MS (ESI) m/z: 177.1 [M+H]$^+$.

3,6-difluoro-2-(3-methyl-4-oxo-quinazolin-6-yl)oxy-benzonitrile

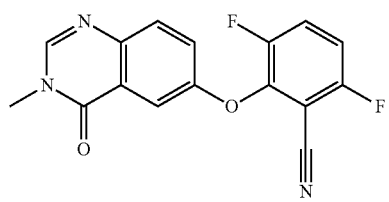 [SMILES: Cn1cnc2ccc(Oc3c(F)ccc(F)c3C#N)cc2c1=O]

Cesium carbonate (3.22 g, 9.79 mmol, Eq: 1.15) was added at rt to a solution of 6-hydroxy-3-methylquinazolin-4-one (1500 mg, 8.51 mmol, Eq: 1.0) in N,N-dimethylformamide (35 mL). The mixture was stirred for 30 min at rt then 2,3,6-trifluorobenzonitrile (1.47 g, 1.08 ml, 9.37 mmol, Eq: 1.1) was added. After 1 h, the reaction was cooled on ice and diluted with water (120 mL). The resultant solid was collected by filtration, washed with iced water (100 mL) and heptane (100 mL) and suction-dried. The solid was taken up in toluene and evaporated to dryness (3×) then dried overnight in vacuo to give the title compound as a light brown solid (2.58 g, 97% yield). MS (ESI) m/z: 314.1 [M+H]+.

(3R)-3-fluoropyrrolidine-1-sulfonamide

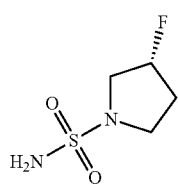

(R)-3-Fluoropyrrolidine hydrochloride (1.8 g, 14.3 mmol, Eq: 1.2) was added to a solution of sulfuric diamide (1.148 g, 11.9 mmol, Eq: 1.0) and triethylamine (2.42 g, 3.33 mL, 23.9 mmol, Eq: 2) in dioxane (10 mL). The reaction was stirred in a sealed tube at 115° C. for 15.5 h then cooled to rt and concentrated in vacuo. The residue was diluted with DCM, evaporated with silica gel to dryness and transferred to a column. Purification by flash chromatography (40 g silica, 80% EtOAc) gave the title compound as a white crystalline solid (1.82 g, 91% yield). MS (ESI) m/z: 169.1 [M+H]$^+$.

(3S)-3-fluoropyrrolidine-1-sulfonamide

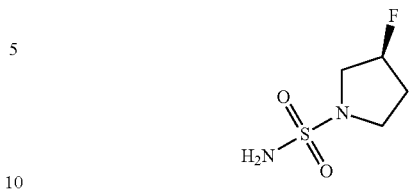

Triethylamine (304 mg, 419 µl, 3.01 mmol, Eq: 2.0) was added to a suspension of sulfuric diamide (146 mg, 1.5 mmol, Eq: 1.0) and (S)-3-fluoropyrrolidine hydrochloride (234 mg, 1.8 mmol, Eq: 1.2) in dioxane (1.3 ml). The reaction was stirred in a sealed tube at 115° C. for 16 h 35 min, then concentrated in vacuo. The residue was diluted with MeOH and evaporated with silica gel to dryness and transferred to a column. Purification by flash chromatography (40 g silica, 0-8% MeOH/DCM) gave the title compound as a light yellow solid (193 mg, 75% yield). MS (ESI) m/z: 169.1 [M+H]$^+$.

(3R)—N-[2-cyano-4-fluoro-3-(3-methyl-4-oxo-quinazolin-6-yl)oxy-phenyl]-3-fluoro-pyrrolidine-1-sulfonamide (Example 1)

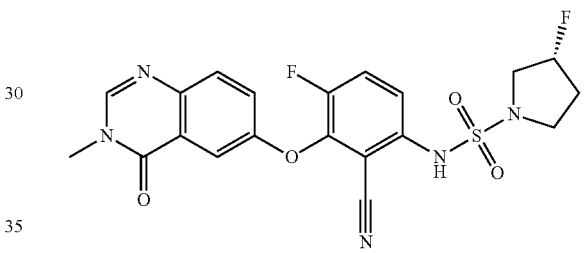

(R)-3-Fluoropyrrolidine-1-sulfonamide (1.26 g, 7.51 mmol, Eq: 2.1) and cesium carbonate (2.56 g, 7.87 mmol, Eq: 2.2) were suspended in dry DMF (10.2 ml) under an argon atmosphere. The reaction was stirred at 50° C. for 30 min. The reaction mixture was cooled to rt and a solution of 3,6-difluoro-2-((3-methyl-4-oxo-3,4-dihydroquinazolin-6-yl)oxy)benzonitrile (1.12 g, 3.58 mmol, Eq: 1.0) in DMF (25.5 ml) was added. The reaction mixture was stirred at 100° C. for 15 h, then concentrated in vacuo. The residue was taken up in sat. aq. NH$_4$Cl (100 mL) and EtOAc (100 mL). The phases were separated, and the aqueous layer was extracted further with 2×100 mL EtOAc. The combined organic layers were washed with water (200 mL) and brine (200 mL), dried (Na$_2$SO$_4$), filtered and concentrated in vacuo. The water layer was back-extracted with EtOAc (3×100 mL). The combined organic extracts were washed with brine (200 mL), dried (Na$_2$SO$_4$), filtered and concentrated in vacuo. The residue was diluted with DCM and MeOH, and concentrated onto silica. Purification by flash chromatography (120 g, 0.5-2% MeOH/DCM) gave an off-white solid which was triturated with 1:1 heptane/DCM (20 mL) with sonication, then dried in vacuo to give the title compound as a colourless solid (1.087 g, 66% yield). MS (ESI) m/z: 426.2 [M+H]$^+$. Chiral SFC: RT=4.594 min [Chiralpak IC column, 4.6×250 mm, 5 µm particle size (Daicel); gradient of 20-40% MeOH containing 0.2% NHEt$_2$ over 8 min; flow: 2.5 mL/min; 140 bar backpressure].

(3S)—N-[2-cyano-4-fluoro-3-(3-methyl-4-oxo-quinazolin-6-yl)oxy-phenyl]-3-fluoro-pyrrolidine-1-sulfonamide (Example 2)

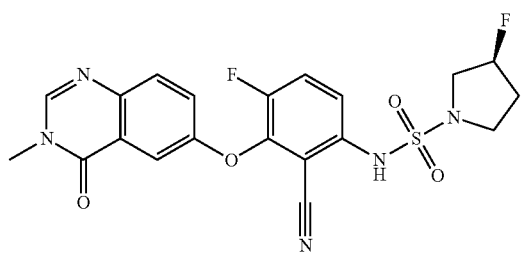 [SMILES: Cn1cnc2ccc(Oc3c(F)ccc(NS(=O)(=O)N4CC[C@H](F)C4)c3C#N)cc2c1=O]

(S)-3-Fluoropyrrolidine-1-sulfonamide (181 mg, 1.08 mmol, Eq: 2.1) was dissolved in DMF (1.6 ml). At rt cesium carbonate (368 mg, 1.13 mmol, Eq: 2.2) was added and the reaction mixture was stirred at 50° C. for 30 min. The reaction mixture was cooled to rt and a solution of 3,6-difluoro-2-((3-methyl-4-oxo-3,4-dihydroquinazolin-6-yl)oxy)benzonitrile (160.8 mg, 513 µmol, Eq: 1.0) in DMF (4 ml) was added. The reaction mixture was stirred at 105° C. for 2 h 50 min then concentrated in vacuo. The residue was taken up in DCM and washed with sat. aq. $NH_4Cl$. The aq. layer was back-extracted twice with DCM. The combined organic layers were dried over $Na_2SO_4$, filtrated and evaporated. The residue (brown oil) was diluted with DCM and transferred to a column. Purification by flash chromatography (80 g, 0-100% EtOAc in DCM) gave a solid which was further purified by SFC to give the title compound as a light yellow solid (119 mg, 50% yield). MS (ESI) m/z: 426.2 $[M+H]^+$. Chiral SFC: RT=4.411 min [Chiralpak IC column, 4.6×250 mm, 5 µm particle size (Daicel); gradient of 20-40% MeOH containing 0.2% $NHEt_2$ over 8 min; flow: 2.5 mL/min; 140 bar backpressure].

The invention claimed is:

1. A compound of Formula (I):

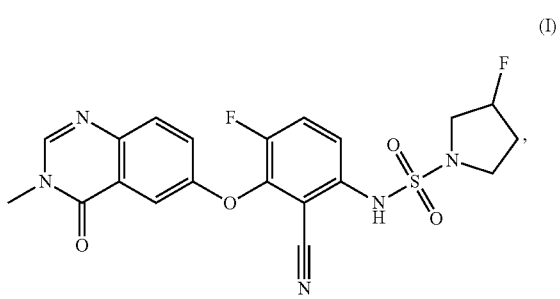 [SMILES: Cn1cnc2ccc(Oc3c(F)ccc(NS(=O)(=O)N4CCC(F)C4)c3C#N)cc2c1=O]

or a pharmaceutically acceptable salt thereof.

2. A pharmaceutical composition comprising the compound according to claim 1, or a pharmaceutically acceptable salt thereof, and a therapeutically inert carrier.

3. A method of treating a cancer selected from thyroid cancer, colorectal cancer, brain cancer, melanoma, and non-small cell lung cancer (NSCLC), the method comprising administering an effective amount of the compound according to claim 1, or a pharmaceutically acceptable salt thereof, to a patient in need thereof.

4. The method of claim 3, wherein the cancer is colorectal cancer.

5. The method of claim 3, wherein the cancer is melanoma.

6. The method of claim 3, wherein the cancer is non-small cell lung cancer (NSCLC).

7. The compound of claim 1, wherein the compound is the compound of formula (I):

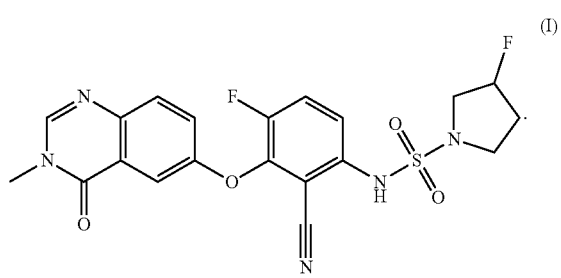 [SMILES: Cn1cnc2ccc(Oc3c(F)ccc(NS(=O)(=O)N4CCC(F)C4)c3C#N)cc2c1=O]

8. A pharmaceutical composition comprising the compound according to claim 7, and a therapeutically inert carrier.

9. A method of treating a cancer selected from thyroid cancer, colorectal cancer, brain cancer, melanoma, and non-small cell lung cancer (NSCLC), the method comprising administering an effective amount of the compound according to claim 7, to a patient in need thereof.

10. The method of claim 9, wherein the cancer is colorectal cancer.

11. The method of claim 9, wherein the cancer is melanoma.

12. The method of claim 9, wherein the cancer is non-small cell lung cancer (NSCLC).

13. The compound of claim 1, wherein the compound is the pharmaceutically acceptable salt of the compound of formula (I).

14. A pharmaceutical composition comprising the compound according to claim 13, and a therapeutically inert carrier.

15. A method of treating a cancer selected from thyroid cancer, colorectal cancer, brain cancer, melanoma, and non-small cell lung cancer (NSCLC), the method comprising administering an effective amount of the compound according to claim 13, to a patient in need thereof.

16. The method of claim 15, wherein the cancer is colorectal cancer.

17. The method of claim 15, wherein the cancer is melanoma.

18. The method of claim 15, wherein the cancer is non-small cell lung cancer (NSCLC).

19. A compound of Formula (Ia):

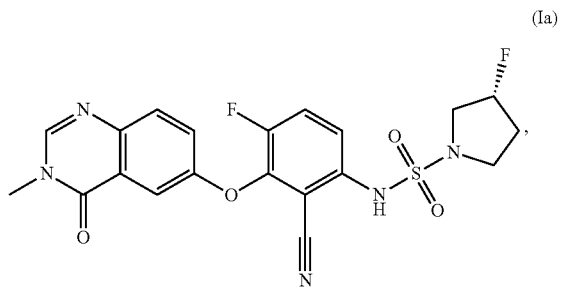 [SMILES: Cn1cnc2ccc(Oc3c(F)ccc(NS(=O)(=O)N4CC[C@@H](F)C4)c3C#N)cc2c1=O]

or a pharmaceutically acceptable salt thereof.

20. A pharmaceutical composition comprising the compound according to claim 19, or a pharmaceutically acceptable salt thereof, and a therapeutically inert carrier.

21. A method of treating a cancer selected from thyroid cancer, colorectal cancer, brain cancer, melanoma, and non-small cell lung cancer (NSCLC), the method comprising administering an effective amount of the compound according to claim 19, or a pharmaceutically acceptable salt thereof, to a patient in need thereof.

22. The method of claim 21, wherein the cancer is colorectal cancer.

23. The method of claim 21, wherein the cancer is melanoma.

24. The method of claim 21, wherein the cancer is non-small cell lung cancer (NSCLC).

25. The compound of claim 19, wherein the compound is the compound of formula (Ia):

(Ia)

26. A pharmaceutical composition comprising the compound according to claim 25, and a therapeutically inert carrier.

27. A method of treating a cancer selected from thyroid cancer, colorectal cancer, brain cancer, melanoma, and non-small cell lung cancer (NSCLC), the method comprising administering an effective amount of the compound according to claim 25, to a patient in need thereof.

28. The method of claim 27, wherein the cancer is colorectal cancer.

29. The method of claim 27, wherein the cancer is melanoma.

30. The method of claim 27, wherein the cancer is non-small cell lung cancer (NSCLC).

31. The compound of claim 19, wherein the compound is the pharmaceutically acceptable salt of the compound of formula (Ia).

32. A pharmaceutical composition comprising the compound according to claim 31, and a therapeutically inert carrier.

33. A method of treating a cancer selected from thyroid cancer, colorectal cancer, brain cancer, melanoma, and non-small cell lung cancer (NSCLC), the method comprising administering an effective amount of the compound according to claim 31, to a patient in need thereof.

34. The method of claim 33, wherein the cancer is colorectal cancer.

35. The method of claim 33, wherein the cancer is melanoma.

36. The method of claim 33, wherein the cancer is non-small cell lung cancer (NSCLC).

37. A compound of Formula (Ib):

(Ib)

or a pharmaceutically acceptable salt thereof.

38. A pharmaceutical composition comprising the compound according to claim 37, or a pharmaceutically acceptable salt thereof, and a therapeutically inert carrier.

39. A method of treating a cancer selected from thyroid cancer, colorectal cancer, brain cancer, melanoma, and non-small cell lung cancer (NSCLC), the method comprising administering an effective amount of the compound according to claim 37, or a pharmaceutically acceptable salt thereof, to a patient in need thereof.

40. The method of claim 39, wherein the cancer is colorectal cancer.

41. The method of claim 39, wherein the cancer is melanoma.

42. The method of claim 39, wherein the cancer is non-small cell lung cancer (NSCLC).

43. The compound of claim 37, wherein the compound is the compound of formula (Ib):

(Ib)

44. A pharmaceutical composition comprising the compound according to claim 43, and a therapeutically inert carrier.

45. A method of treating a cancer selected from thyroid cancer, colorectal cancer, brain cancer, melanoma, and non-small cell lung cancer (NSCLC), the method comprising administering an effective amount of the compound according to claim 43, to a patient in need thereof.

46. The method of claim 45, wherein the cancer is colorectal cancer.

47. The method of claim 45, wherein the cancer is melanoma.

48. The method of claim 45, wherein the cancer is non-small cell lung cancer (NSCLC).

49. The compound of claim 37, wherein the compound is the pharmaceutically acceptable salt of the compound of formula (Ib).

50. A pharmaceutical composition comprising the compound according to claim 49, and a therapeutically inert carrier.

51. A method of treating a cancer selected from thyroid cancer, colorectal cancer, brain cancer, melanoma, and non-small cell lung cancer (NSCLC), the method comprising administering an effective amount of the compound according to claim 49, to a patient in need thereof.

52. The method of claim 51, wherein the cancer is colorectal cancer.

53. The method of claim 51, wherein the cancer is melanoma.

54. The method of claim 51, wherein the cancer is non-small cell lung cancer (NSCLC).

* * * * *